United States Patent
Lee et al.

(10) Patent No.: US 9,119,948 B2
(45) Date of Patent: Sep. 1, 2015

(54) OCCLUSIVE IMPLANTS FOR HOLLOW ANATOMICAL STRUCTURES, DELIVERY SYSTEMS, AND RELATED METHODS

(71) Applicant: Covidien LP, Mansfield, MA (US)

(72) Inventors: Stephen Lee, San Jose, CA (US); Walter Stevens, San Jose, CA (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 13/771,133

(22) Filed: Feb. 20, 2013

(65) Prior Publication Data
US 2014/0236127 A1    Aug. 21, 2014

(51) Int. Cl.
| A61B 17/122 | (2006.01) |
| A61M 39/10 | (2006.01) |
| A61B 17/12 | (2006.01) |
| A61B 17/00 | (2006.01) |

(52) U.S. Cl.
CPC ............ *A61M 39/1011* (2013.01); *A61B 17/12* (2013.01); *A61B 17/1214* (2013.01); *A61B 17/12031* (2013.01); *A61B 17/12109* (2013.01); *A61B 2017/00477* (2013.01); *A61B 2017/00623* (2013.01); *A61B 2017/1205* (2013.01); *A61B 2017/12054* (2013.01)

(58) Field of Classification Search
CPC ...................... A61B 17/12022; A61B 17/1214; A61B 2017/1205; A61B 17/221; A61B 17/12172
See application file for complete search history.

(56) References Cited

U.S. PATENT DOCUMENTS

| 765,879 | A | * | 7/1904 | Campbell | 606/198 |
| 4,788,966 | A | | 12/1988 | Yoon | |
| 5,029,908 | A | * | 7/1991 | Belisaire | 285/323 |
| 5,089,006 | A | * | 2/1992 | Stiles | 623/1.1 |
| 5,098,437 | A | | 3/1992 | Kashuba et al. | |
| 5,171,243 | A | | 12/1992 | Kashuba et al. | |
| 5,226,911 | A | | 7/1993 | Chee et al. | |
| 5,234,458 | A | * | 8/1993 | Metais | 606/200 |
| 5,304,194 | A | | 4/1994 | Chee et al. | |
| 5,334,210 | A | * | 8/1994 | Gianturco | 606/151 |
| 5,382,259 | A | | 1/1995 | Phelps et al. | |

(Continued)

FOREIGN PATENT DOCUMENTS

| WO | WO 00/44428 | 8/2000 |
| WO | WO 2004/087235 | 10/2004 |

(Continued)

OTHER PUBLICATIONS

Sharafuddin et al., "The Nitinol Vascular Occlusion Plug: Preliminary Experimental Evaluation in Peripheral Veins" Journal of Vascular and Interventional Radiology, vol. 10, Jan. 1999, pp. 23-27.

(Continued)

*Primary Examiner* — Scott Medway
(74) *Attorney, Agent, or Firm* — Thomas M. Johnston, Esq.

(57) ABSTRACT

An implant and delivery system including a female coupler at a proximal end of the implant and a male coupler at a distal end of an elongate tubular delivery member. The male coupler is insertable within the female coupler and expandable under the influence of an elongate control member that is slidable within the tubular delivery member. Expansion of the male coupler locks the implant to the tubular delivery member. Withdrawal of the control member unlocks the implant from the tubular delivery member, enabling placement of the implant within a body.

35 Claims, 12 Drawing Sheets

(56) References Cited

U.S. PATENT DOCUMENTS

| | | | |
|---|---|---|---|
| 5,417,696 A | 5/1995 | Kashuba et al. | |
| 5,423,849 A | 6/1995 | Engelson et al. | |
| 5,522,822 A | 6/1996 | Phelps et al. | |
| 5,601,600 A * | 2/1997 | Ton | 606/206 |
| 5,609,608 A * | 3/1997 | Benett et al. | 606/205 |
| 5,645,558 A | 7/1997 | Horton | |
| 5,649,949 A | 7/1997 | Wallace et al. | |
| 5,669,931 A | 9/1997 | Kupiecki et al. | |
| 5,683,399 A | 11/1997 | Jones | |
| 5,690,666 A | 11/1997 | Berenstein et al. | |
| 5,718,711 A | 2/1998 | Berenstein et al. | |
| 5,749,894 A | 5/1998 | Engelson | |
| 5,752,973 A * | 5/1998 | Kieturakis | 606/207 |
| 5,766,219 A | 6/1998 | Horton | |
| 5,792,154 A | 8/1998 | Doan et al. | |
| 5,810,864 A * | 9/1998 | Schaller | 606/170 |
| 5,826,587 A | 10/1998 | Berenstein et al. | |
| 5,843,118 A | 12/1998 | Sepetka et al. | |
| 5,853,420 A * | 12/1998 | Chevillon et al. | 606/200 |
| 5,891,130 A * | 4/1999 | Palermo et al. | 606/1 |
| 5,911,731 A | 6/1999 | Pham et al. | |
| 5,935,145 A | 8/1999 | Villar et al. | |
| 5,968,064 A * | 10/1999 | Selmon et al. | 606/189 |
| 5,976,162 A | 11/1999 | Doan et al. | |
| 6,024,754 A | 2/2000 | Engelson | |
| 6,059,829 A | 5/2000 | Schläpfer et al. | |
| 6,090,125 A | 7/2000 | Horton | |
| 6,156,061 A | 12/2000 | Wallace et al. | |
| 6,168,622 B1 | 1/2001 | Mazzocchi | |
| 6,187,027 B1 | 2/2001 | Mariant et al. | |
| 6,193,739 B1 * | 2/2001 | Chevillon et al. | 606/200 |
| 6,238,415 B1 * | 5/2001 | Sepetka et al. | 606/213 |
| 6,254,612 B1 * | 7/2001 | Hieshima | 606/108 |
| 6,287,318 B1 | 9/2001 | Villar et al. | |
| 6,322,576 B1 | 11/2001 | Wallace et al. | |
| 6,346,117 B1 | 2/2002 | Greenhalgh | |
| 6,383,193 B1 * | 5/2002 | Cathcart et al. | 606/108 |
| 6,391,037 B1 | 5/2002 | Greenhalgh | |
| 6,425,914 B1 | 7/2002 | Wallace et al. | |
| 6,436,119 B1 * | 8/2002 | Erb et al. | 606/198 |
| 6,458,119 B1 | 10/2002 | Berenstein et al. | |
| 6,585,754 B2 | 7/2003 | Wallace et al. | |
| 6,634,361 B1 | 10/2003 | Nikolchev et al. | |
| 6,800,085 B2 * | 10/2004 | Selmon et al. | 606/198 |
| 6,860,893 B2 | 3/2005 | Wallace et al. | |
| 6,936,058 B2 * | 8/2005 | Forde et al. | 606/200 |
| 7,244,261 B2 | 7/2007 | Lorenzo et al. | |
| 7,247,159 B2 | 7/2007 | Lorenzo et al. | |
| 7,572,274 B2 | 8/2009 | Yassinzadeh | |
| 7,608,091 B2 * | 10/2009 | Goldfarb et al. | 606/215 |
| 7,651,521 B2 * | 1/2010 | Ton et al. | 623/1.12 |
| 7,695,484 B2 | 4/2010 | Wallace et al. | |
| 7,857,840 B2 | 12/2010 | Krebs et al. | |
| 7,871,419 B2 * | 1/2011 | Devellian et al. | 606/157 |
| 7,896,899 B2 | 3/2011 | Patterson et al. | |
| 7,955,344 B2 | 6/2011 | Finitsis | |
| 7,955,345 B2 | 6/2011 | Kucharezyk et al. | |
| 8,007,509 B2 | 8/2011 | Buiser et al. | |
| 8,016,869 B2 * | 9/2011 | Nikolchev | 623/1.11 |
| 8,043,321 B2 | 10/2011 | Elliott | |
| 8,333,796 B2 * | 12/2012 | Tompkins et al. | 623/1.11 |
| 8,414,644 B2 * | 4/2013 | Quadri et al. | 623/2.11 |
| 8,500,773 B2 * | 8/2013 | Nardone et al. | 606/200 |
| 8,764,848 B2 * | 7/2014 | Callaghan et al. | 623/23.72 |
| 2002/0116024 A1 * | 8/2002 | Goldberg et al. | 606/200 |
| 2003/0004568 A1 | 1/2003 | Ken et al. | |
| 2003/0032976 A1 | 2/2003 | Boucek | |
| 2003/0093111 A1 | 5/2003 | Ken et al. | |
| 2005/0149109 A1 | 7/2005 | Wallace et al. | |
| 2005/0277978 A1 | 12/2005 | Greenhalgh | |
| 2006/0020286 A1 | 1/2006 | Niermann | |
| 2006/0079926 A1 | 4/2006 | Desai et al. | |
| 2006/0155324 A1 | 7/2006 | Porter et al. | |
| 2006/0178696 A1 | 8/2006 | Porter et al. | |
| 2006/0178697 A1 | 8/2006 | Carr-Brendel | |
| 2006/0276831 A1 | 12/2006 | Porter et al. | |
| 2007/0078479 A1 | 4/2007 | Belenkaya et al. | |
| 2007/0239194 A1 | 10/2007 | Tran et al. | |
| 2007/0239199 A1 | 10/2007 | Jayaraman | |
| 2008/0097508 A1 | 4/2008 | Jones et al. | |
| 2008/0114391 A1 | 5/2008 | Dieck et al. | |
| 2008/0125807 A1 | 5/2008 | Wallace et al. | |
| 2008/0195139 A1 | 8/2008 | Donald et al. | |
| 2008/0221554 A1 | 9/2008 | O'Connor et al. | |
| 2008/0262528 A1 | 10/2008 | Martin | |
| 2009/0105712 A1 | 4/2009 | Dauster et al. | |
| 2009/0112219 A1 | 4/2009 | Daniels et al. | |
| 2009/0131972 A1 | 5/2009 | Wallace et al. | |
| 2009/0254190 A1 | 10/2009 | Gannoe et al. | |
| 2009/0270978 A1 | 10/2009 | Virkler et al. | |
| 2010/0016885 A1 | 1/2010 | Eidenschink et al. | |
| 2010/0036412 A1 | 2/2010 | Porter et al. | |
| 2010/0114105 A1 | 5/2010 | Butters et al. | |
| 2010/0217303 A1 | 8/2010 | Goodwin | |
| 2010/0292704 A1 | 11/2010 | Stoffel et al. | |
| 2010/0324586 A1 * | 12/2010 | Miles et al. | 606/198 |
| 2011/0009872 A1 | 1/2011 | Mistry et al. | |
| 2011/0054485 A1 | 3/2011 | Kullas et al. | |
| 2011/0118777 A1 | 5/2011 | Patterson et al. | |
| 2011/0184455 A1 | 7/2011 | Keeley et al. | |
| 2011/0202085 A1 | 8/2011 | Loganathan et al. | |
| 2011/0213405 A1 | 9/2011 | Porter et al. | |
| 2011/0230908 A1 | 9/2011 | Finitsis | |
| 2011/0270261 A1 | 11/2011 | Mast et al. | |
| 2011/0295303 A1 | 12/2011 | Freudenthal | |
| 2011/0319926 A1 | 12/2011 | Becking et al. | |
| 2013/0178889 A1 * | 7/2013 | Miles et al. | 606/200 |

FOREIGN PATENT DOCUMENTS

| | | |
|---|---|---|
| WO | WO 2006/111945 | 10/2006 |
| WO | WO 2008/127525 | 10/2008 |

OTHER PUBLICATIONS

European Search Report on related EP Application No. 14151313.5 from International Searching Authority (EPO) dated May 20, 2014.

Extended Search Report from counterpart European Patent Application No. 14151313.5, dated Nov. 7, 2014, 12 pp.

* cited by examiner

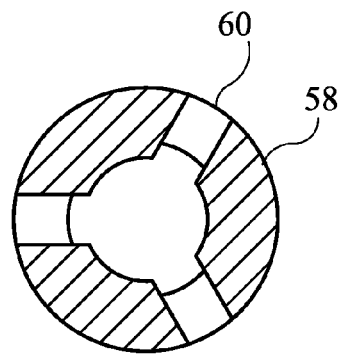
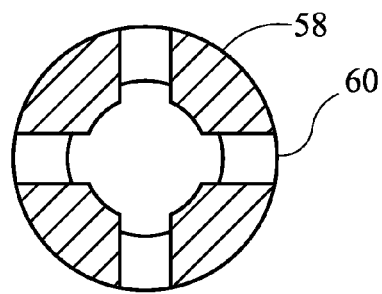
FIG. 5A  FIG. 5B
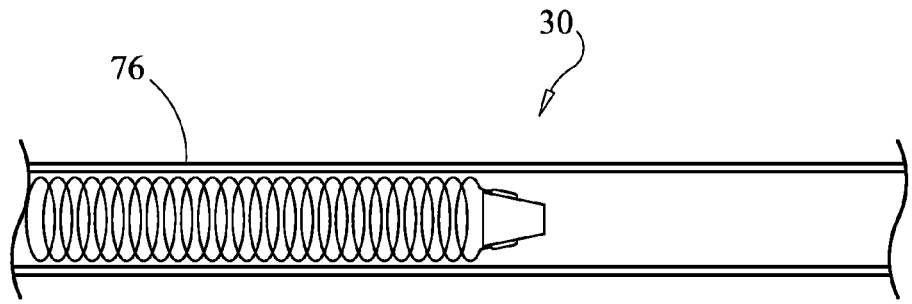
FIG. 6
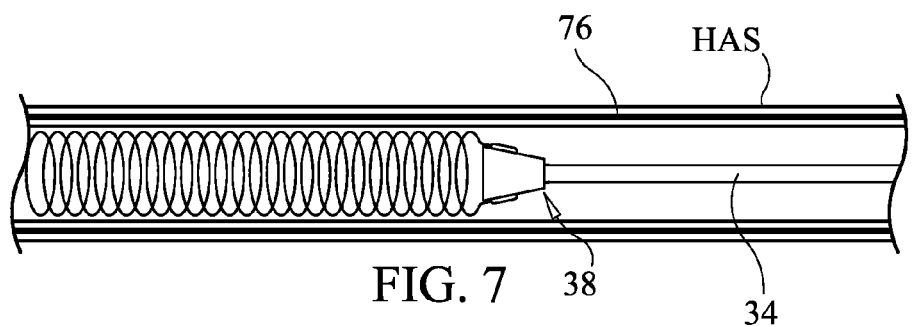
FIG. 7

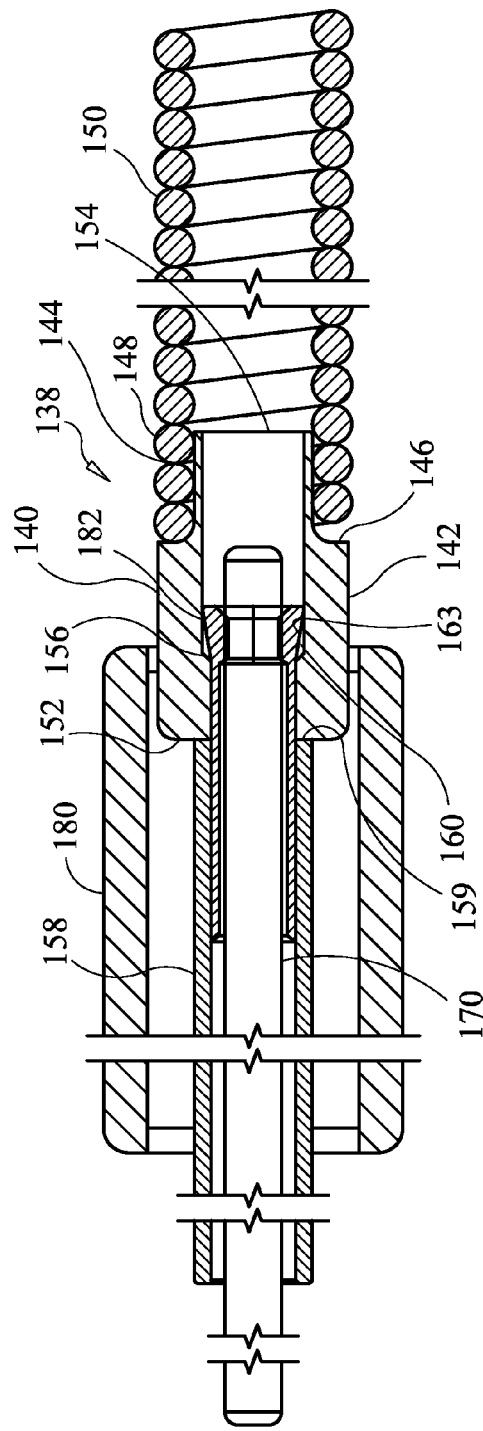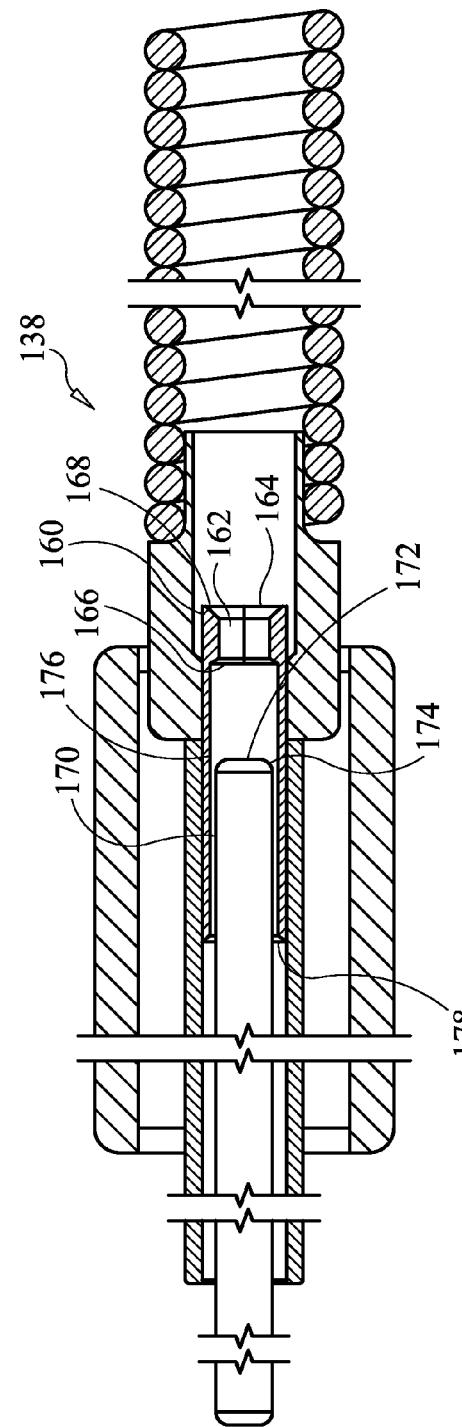

OCCLUSIVE IMPLANTS FOR HOLLOW ANATOMICAL STRUCTURES, DELIVERY SYSTEMS, AND RELATED METHODS

TECHNICAL FIELD

The present embodiments relate to occlusive implants for hollow anatomical structures, delivery devices therefor, and related methods.

BACKGROUND

Hollow anatomical structures (HAS) may include, without limitation, veins, arteries, gastric structures, coronary structures, pulmonary structures, and tubular structures associated with reproductive organs. These and other HAS provide various functions throughout the body, but in some instances require intervention to correct a physical defect or ailment.

For example, the venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and enables only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional failure of other valves distal to the first incompetent valve. Two venous conditions or symptoms that often result from valve failure are varicose veins and more symptomatic chronic venous insufficiency (CVI).

Another condition that can result from valve failure is pelvic congestion syndrome (PCS). It is believed that PCS is associated with varicose veins in the pelvis (lower abdomen and groin). Often, the varicose veins develop during pregnancy and continue to progress in size. The syndrome is associated with constant dull pelvic pain, pressure and heaviness. One method of alleviating the pain and cosmetic issues due to varicose veins, CVI or PCS is to occlude the vein to divert blood flow to other, healthy veins.

SUMMARY

The preferred embodiments relate generally to apparatus and methods for introducing occlusive implants into a hollow anatomical structure (HAS). Hollow anatomical structures particularly suited to occlusion by the present apparatus and methods include, but are not limited to, veins, particularly pelvic veins. The various embodiments of the present occlusive implants for hollow anatomical structures, delivery devices, and related methods have several features. Without limiting the scope of the present embodiments as expressed by the claims that follow, their features now will be discussed briefly. After considering this discussion, and particularly after reading the section entitled "Detailed Description," one will understand how the features of the present embodiments provide the advantages described herein.

One of the present embodiments comprises apparatus for delivering an occlusive implant in a hollow anatomical structure. The apparatus comprises an elongate flexible delivery tube having a proximal end and a distal end, and defining an internal delivery tube lumen having an inner lumen diameter. The apparatus further comprises a male coupler at the distal end of the delivery tube and defining an infernal male coupler lumen. The male coupler includes a plurality of cantilevered flexible legs each including a distal end. Each of the legs includes an internal surface that defines at least a portion of the male coupler lumen and tapers inwardly toward the distal end of each leg such that an interior diameter of the made coupler lumen decreases in the proximal-to-distal direction. The male coupler defines a constant outer diameter over its length. The apparatus further comprises an elongate control member received within the delivery tube lumen of the delivery tube and translatable therein proximally and distally. The control member has an outer diameter less than the inner diameter of the delivery tube lumen and the internal male coupler lumen but greater than the interior diameter of the male coupler lumen adjacent the distal end of the legs, such that when the control member is advanced distally within the male coupler lumen the control member contacts the internal surfaces of the legs to cause them to flex outwardly.

Another of the present embodiments comprises a system for occluding a hollow anatomical structure. The system comprises an occlusive implant including an occluding portion and a tubular female coupler. The female coupler defines a female coupler lumen whose internal diameter increases in the proximal-to-distal direction. The system further comprises an elongate flexible delivery tube defining a delivery tube lumen and having a distal end comprising a male coupler. The male coupler defines a male coupler lumen and includes a plurality of cantilevered flexible legs configured to be received within the female coupler lumen. Each of the legs includes an internal surface that defines at least a portion of the male coupler lumen. The system further comprises an elongate control member received within the delivery tube lumen and translatable therein proximally and distally. The control member has an outer diameter greater than an interior diameter of the male coupler lumen adjacent a distal end of the male coupler lumen, such mat when the control member is advanced distally within the male coupler lumen the control member contacts the internal surfaces of the flexible legs to cause the flexible legs to flex outwardly and contact an inner surface of the female coupler lumen to releasably secure the implant to the delivery device.

Another of the present embodiments comprises a method for delivering an occlusive implant to a treatment site in a vessel of a body using an elongate flexible delivery device. The method comprises accessing vasculature of the body at an access site remote from the treatment site, and introducing the implant and the delivery device into the vasculature at the access site. The method further comprises advancing the implant and the delivery device through the vasculature toward the treatment site, and positioning the implant as desired at the treatment site. The method further comprises expanding the implant to contact an interior wall of the vessel and at least partially occlude the vessel. The method further comprises disengaging the implant from the delivery device and withdrawing the delivery device. The implant includes a tubular female coupler defining a female coupler lumen. The delivery device includes a distal end comprising a male coupler, and the male coupler is received within the female coupler lumen. The male coupler defines a male coupler lumen therethrough and includes a plurality of cantilevered flexible legs extending distally. Disengaging the implant from the delivery device comprises withdrawing an elongate flexible control member received within a lumen of the delivery device and the male coupler lumen. The control member has an outer diameter greater than an interior diameter of the male coupler lumen at a distal end of the male coupler, such that as the control member is withdrawn from the male coupler lumen radially outwardly directed force is released from internal surfaces of the legs to cause the legs to relax and retract radially inwardly.

BRIEF DESCRIPTION OF THE DRAWINGS

The various embodiments of the present occlusive implants for hollow anatomical structures, delivery devices, and related methods now will be discussed in detail with an emphasis on highlighting the advantageous features. These embodiments depict the novel and non-obvious occlusive implants for hollow anatomical structures, delivery devices, and related methods shown in the accompanying drawings, which are for illustrative purposes only. These drawings include the following figures, in which like numerals indicate like parts:

FIGS. 5A and 5B are cross-sectional views of two different embodiments of the male coupler of FIG. 4, taken along the line 5-5;

FIGS. 6-9 are schematic side elevation views of one embodiment of a method of using the delivery system of FIG. 1;

FIG. 14 is a detail cross-sectional view of another embodiment of the present delivery systems for occlusive implants, showing the male and female couplers in an engaged and locked position;

FIG. 15 is a detail cross-sectional view of the system of FIG. 14, showing the male and female couplers in an engaged and unlocked position;

DETAILED DESCRIPTION

Figure 1:
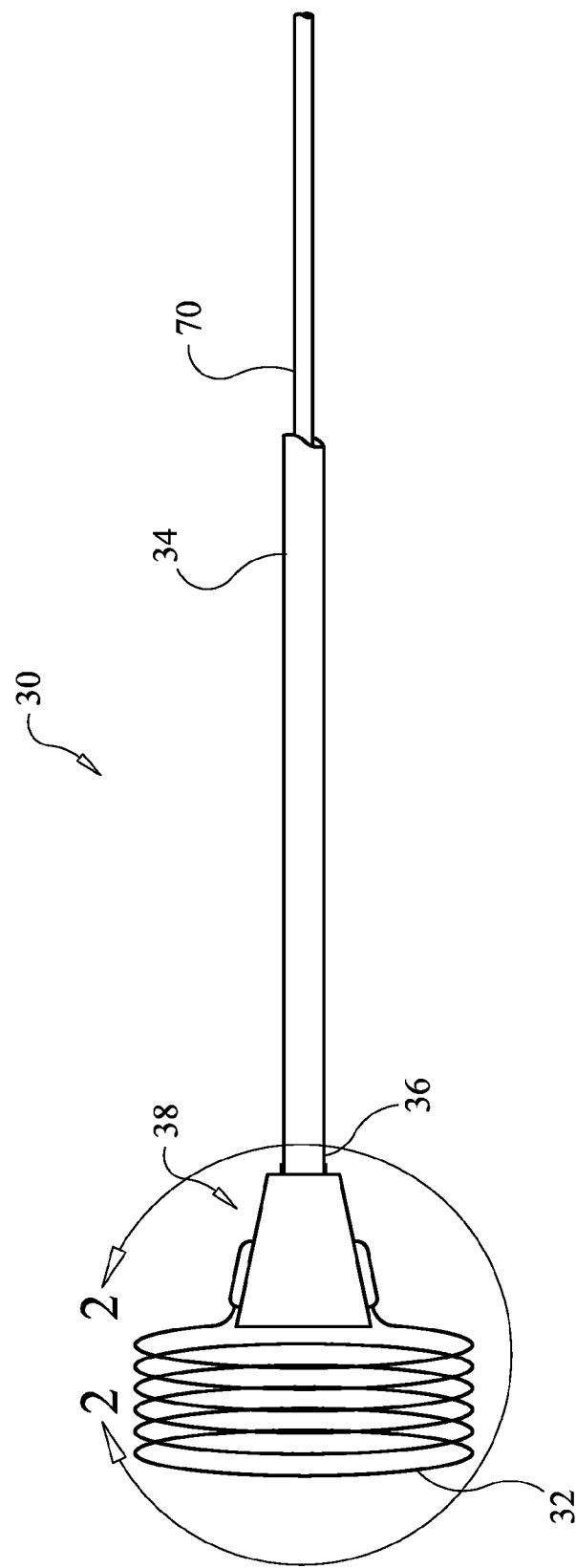
FIG. 1 is a schematic side elevation view of one embodiment of the present delivery systems for occlusive implants.

The following detailed description describes the present embodiments with reference to the figures. In the figures, reference numbers label elements of the present embodiments. These reference numbers are reproduced below in connection with the discussion of the corresponding features.

The embodiments of the present occlusive implants for hollow anatomical structures, delivery devices, and related methods are described below with reference to the figures. These figures, and their written descriptions, indicate that certain components of the apparatus are formed integrally, and certain other components are formed as separate pieces. Components shown and described herein as being formed integrally may in alternative embodiments be formed as separate pieces. Components shown and described herein as being formed as separate pieces may in alternative embodiments be formed integrally. Further, as used herein the term integral describes a single unitary piece.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

FIGS. 1-4 illustrate one embodiment of a delivery system 30 for occlusive implants. For example, the system 30 can be used to deliver an occlusive implant 32 to numerous locations within the body, including, without limitation, veins, arteries, gastric structures, coronary structures, pulmonary structures, and tubular structures associated with reproductive organs. The present embodiments are not limited to any particular procedure, or to use in any particular area of the body. In general, the delivery tube 34 is connected to an occlusive implant 32 by a coupler 38. The coupler 38 includes a female coupler 40 and a male coupler 56, both of which define internal lumens. A control member 70 translates distally and proximally within a lumen 72 defined by the delivery tube 34 to move the female and male couplers 40, 56 between engaged and disengaged configurations.

Various types of occlusive implants may be used with the present delivery system and methods. For example, one type of vascular occlusive implant 32 that may be used with the present embodiments is an embolic coil. A typical embolic coil begins as a length of straight wire that is wrapped around a first cylindrical mandrel in a helical pattern, and is then heat treated to assume a permanent coiled shape. This step is known as "primary wind." The coil is then wrapped around a second cylindrical mandrel, again in a helical pattern, and then heat treated to assume a permanent coiled shape. This step is known as "secondary wind," and produces a double-coiled wire. That is, from a distance the coil appears to be an ordinary coiled length of wire, but upon closer inspection, each coil is itself made up coiled wire. Regardless of the type, however, the occlusive implant 32 may be deployed within a vessel, after which blood clots on the implant 32 and forms a thrombus. The thrombus forms an occlusion that seals off the vessel.

With reference to FIG. 1, the illustrated embodiment of the system 30 includes an elongate flexible delivery tube 34 having a distal end 36 that is releasably connected to the occlusive implant 32 by a coupler 38. In the illustrated embodiment, the implant 32 may be a tubular wire mesh coil, embodiments of which are described below. However, the present delivery system 30 is not limited to any particular type of implant, and can be used with implants such as stents, and embolic coils.

Figure 2:
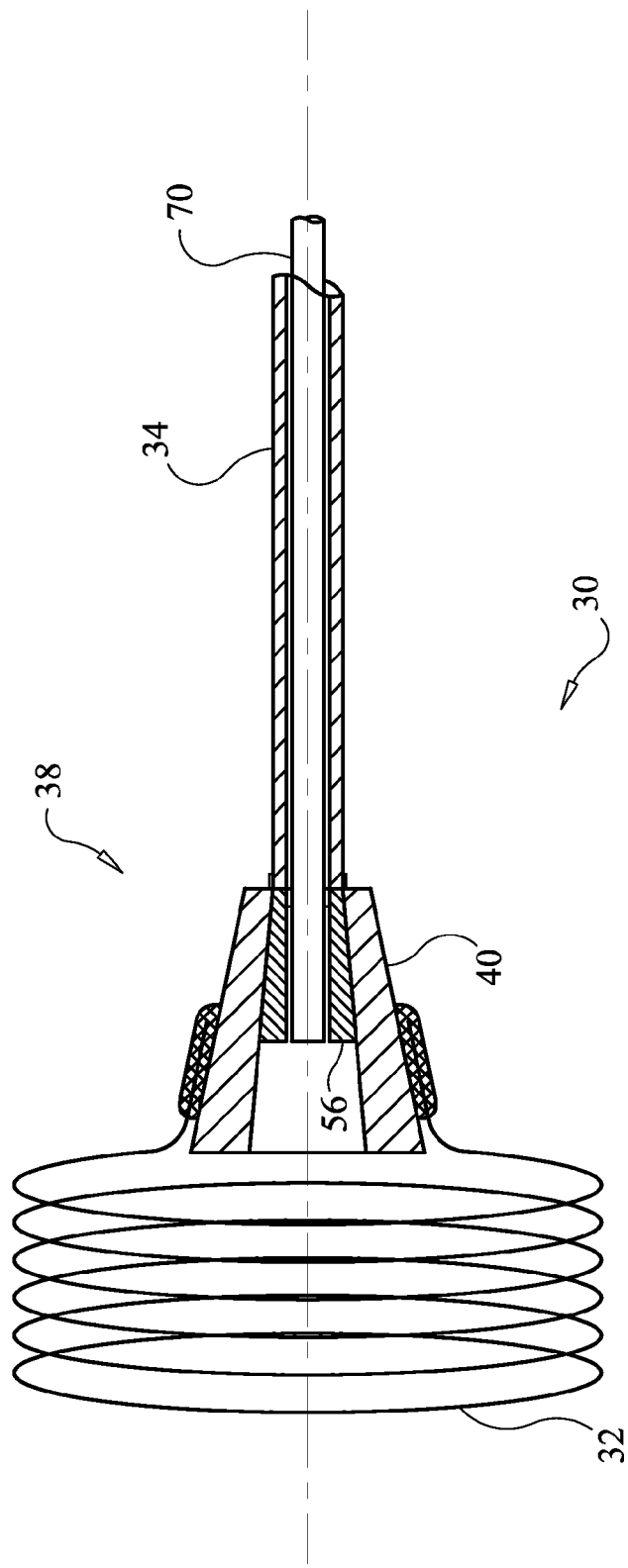
FIG. 2 is a detail cross-sectional view of the portion of FIG. 1 indicated by the circle 2-2, showing the male and female couplers in an engaged and locked position.
Figure 4:
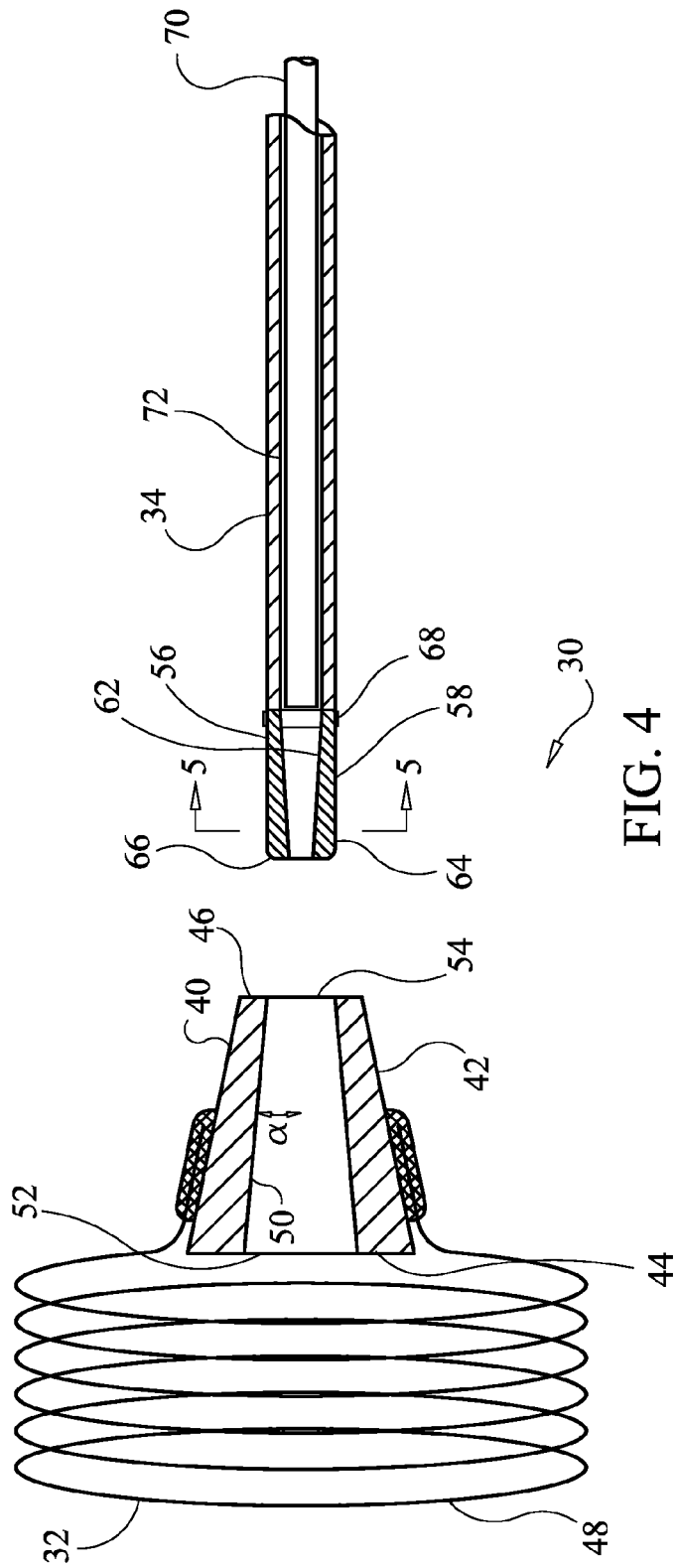
FIG. 4 is a schematic side elevation view of the system of FIG. 2, showing the male and female couplers in a disengaged position.

FIG. 2 illustrates a cross-sectional detail view of the coupler 38 with the delivery tube 34 and the implant 32 secured to one another. FIG. 4 illustrates a cross-sectional detail view of the coupler 38 with the delivery tube 34 and the implant 32 detached from one another. With reference to FIG. 4, the implant 32 includes a female coupler 40 at its proximal end. The female coupler 40 may be conical and tubular. An outer surface 42 of the female coupler 40 may include a smooth taper that extends from a relatively wider distal end 44 to a relatively narrower proximal end 46. Further, a wall thickness of the female coupler 40 may increase a small amount in the proximal-to-distal direction. The outer surface 42 of the female coupler 40 adjoins a main body 48 of the implant 32 such that the main body 48 extends distally from the female coupler 40. The main body 48 may be secured to the female coupler 40 by any conventional technique, such as for example crimping, adhesive, laminating, ultrasonic welding, or laser spot welding.

Where the implant 32 is a coil or a wire mesh, the main body 48 may be constructed of a metal or a metal alloy. Example metals include stainless steel, titanium, or any other metal. The main body 48 may also be constructed of a shape memory alloy, such as a platinum alloy, nitinol, or any other shape memory alloy.

The female coupler 40 further includes a smoothly tapering inner surface 50 that extends from a relatively wider distal opening 52 to a relatively narrower proximal opening 54. However, when the outer surface 42 of the female couple tapers, the taper angles of the inner and outer surfaces 42, 50 may be unequal, such that a wall thickness of the female coupler 40 increases a small amount in the proximal-to-distal direction. The taper angle of the inner surface is constant over its length, and is equal to $\alpha$. In various embodiments, the value of a, as measured from a longitudinal axis of the female coupler 40, may be between about 2° and about 15°, such as between about 5° and about 10°.

The female coupler 40 may be constructed of any suitable biocompatible material, such as, for example, one or more polymers, metals, or ceramics. Non-limiting examples of polymers from which the female coupler 40 may be constructed include nylon, polyethylene, polyurethane, ethylene-vinyl acetate (EVA), polyether block amide (PEBAX), acrylonitrile butadiene styrene (ABS), polyether ether ketone (PEEK), polytetrafluoroethylene (PTFE), and thermoplastic polyetherimide (ULTEM). Non-limiting examples of metals from which the female coupler 40 may be constructed include stainless steel, titanium, and cobalt-chromium. Non-limiting examples of ceramics from which the female coupler 40 may be constructed include porcelain, alumina, hydroxyapatite, and zirconia.

With reference to FIG. 4, the coupler 38 further includes a male coupler 56. The male coupler 56, which may also be referred to as an expandable collet, comprises a plurality of distally extending cantilevered legs 58. FIGS. 5A and 5B are cross-sectional views of two exemplary embodiments of the male coupler 56 taken through the line 5-5 in FIG. 4. As shown, the number of legs 58 in the male coupler 56 may be, for example, three (FIG. 5A) or four (FIG. 5B), or any other number. The legs 58 are defined by gaps 60 between adjacent legs 58.

With reference to FIG. 4, the male coupler 56 is a discrete component that is joined to the delivery tube 34. In the illustrated embodiment, the junction of the male coupler 56 and the delivery tube 34 comprises a butt joint. However, in other embodiments the junction may comprise any other type of joint. Further, in still other embodiments the male coupler 56 may be integral with the delivery tube 34, i.e. not a discrete component. In embodiments where the male coupler 56 is a discrete component, it may be joined to the delivery tube 34 by any suitable process, such as, for example, laser spot welding, ultrasonic welding, and with an adhesive.

With continued reference to FIG. 4, inner surfaces 62 of the legs 58 include an inward taper, such that an interior diameter of the male coupler 56 decreases in the proximal-to-distal direction. In the illustrated embodiment, the taper angle of the legs 58 may be equal to $-\alpha$, i.e. the inverse of the taper angle $\alpha$ of the female coupler 40. In such an embodiment, the legs 58 may bow outwardly such that outer surfaces 64 of the legs 58 abut the inner surface 50 of the female coupler 40 over the entire length of each leg 58 (FIG. 2) when engaged, as described further below. In other embodiments, the taper angle of the legs 58 may be equal to any other value.

The male coupler 56 may be constructed of any suitable biocompatible material that is flexible and resilient, such as one or more polymers. Non-limiting examples of polymers from which the male coupler 56 may be constructed include nylon, polyethylene, polyurethane, ethylene-vinyl acetate (EVA), polyether block amide (PEBAX), acrylonitrile butadiene styrene (ABS), polyether ether ketone (PEEK), polytetrafluoroethylene (PTFE), and thermoplastic polyetherimide (ULTEM). In certain embodiments, the male and female couplers 40, 56 may be constructed of one or more hard plastic materials. Hard plastics provide low friction, reducing the likelihood that the female and male couplers 40, 56 will become stock to one another, which would inhibit the ability of the male coupler 56 to withdraw from the female coupler 40 as the implant 32 is being positioned. Plastics also make the delivery system 30 compatible with magnetic resonance imaging (MRI), as metals tend to heat up to undesirable levels under MRI.

With further reference to FIG. 4, an outer diameter of the male coupler 56 is approximately the same as an inner diameter of the female coupler 40 at its proximal opening 54, with a slight clearance. Such a configuration provides for tighter engagement of the female and male couplers 40, 56, since it enables the legs 58 to bear against the inner surface 50 of the female coupler 40 over their entire lengths when the female and male couplers 40, 56 are engaged and the legs 58 are expanded, as in FIG. 2. Distal outer edges 66 of the male coupler 56 may be tapered, beveled, or rounded, as shown in FIG. 4, to help guide the male coupler 56 into the proximal opening 54 of the female coupler 40.

The male coupler 56 or delivery tube 34 may further include a position limber 68 having an outer diameter larger than the diameter of the proximal opening 54 of the female coupler. When the male coupler 56 is inserted into the female coupler 40, the position limiter 68 bears against a proximal surface of the female coupler 40 around the proximal opening 54, limiting a length of penetration of the male coupler 56 into the female coupler 40. The position limiter 68 is preferably positioned at a point along the length of the male coupler 56 or delivery tube 34 such that a length of the legs 53 extending distally of the position limiter 68 is adequate to retain sufficient flexibility in the legs 58 so that they can perform their intended function of bowing radially outwardly. For example, the position limiter 68 may be located at or near the junction of the delivery tube 34 and the male coupler 56.

In one embodiment, the position limiter 68 may comprise a distal face of the delivery tube 34, wherein the delivery tube 34 has a larger outer diameter than the male coupler 56. In another embodiment, the position limiter 68 may comprise a discrete piece secured to the delivery tube 34 and/or the male coupler 56. For example, the position limiter 68 may comprise a ring having an interior diameter substantially equal to the outer diameter of the delivery tube 34 and/or the male coupler 56, and secured to the exterior of the delivery tube 34 and/or the male coupler 56. Example techniques for securing the discrete position limiter 68 to the delivery tube 34 and/or the male coupler 56 include, without limitation, laser spot welding, ultrasonic welding, and adhesive.

With further reference to FIGS. 1 and 4, the delivery system 30 farther comprises a control member 70, which is slidably received within a lumen 72 of the delivery tube 34. An outer diameter of the control member 70 is slightly smaller than an inner diameter of the lumen 72, and preferably small enough relative to the lumen 72 that any bends in the delivery tube 34 that might result from the delivery system 30 spanning tortuous vasculature during a delivery procedure do not substantially adversely affect the slidability of the control member 70 within the lumen 72. Further, the outer diameter of the control member 70 is greater than at least a minimum inner diameter of the male coupler 56, wherein, a minimum diameter is generally at the distal end of the male coupler and a largest diameter is generally at the proximal end. The control member 70 thus forces the flexible legs 58 to flex outwardly when it is advanced within the lumen 72 such that a distal end 74 of the control member 70 resides within the male coupler 56, as shown in FIG. 2. The diameter of the control member 70 is preferably selected to enable the legs 58 to contact the inner surface 50 of the female coupler 40 over their entire lengths, again as shown in FIG. 2.

Aspects of the male coupler 56, female coupler 40, and the control member 70 are preferably selected so that no plastic deformation occurs within the male coupler 56 when the legs 58 flex outwardly under the influence of the control member 70. The flexible legs 58 will thus return, to their at rest position as the control member 70 is withdrawn from the male coupler 56. This feature enables the implant 32 to be repeatedly recaptured by the male coupler 56 during the implant 32 positioning procedure, so that the implant 32 can be repositioned if necessary. For example, the following parameters may affect whether the legs 58 plastically deform when flexed: the taper angle of the male coupler 56 and/or the female coupler 40, the material(s) of the male coupler 56, the lengths of the legs 58, and/or the thickness of the legs 58 at their area of flexure.

One embodiment of a procedure for implanting an implant 32 using the system 30 of FIGS. 1-4 is illustrated schematically in FIGS. 6-9. FIG. 6 illustrates the system 30 enclosed in a delivery sheath 76. In the illustrated embodiment, the delivery sheath 76 includes an inner diameter that is less than an expanded diameter of the implant 32. The implant 32 is thus compressed within the sheath 76. In this configuration, the engagement of the female and male couplers 40, 56 is as shown in FIG. 2, with the control member 70 advanced distally such that the male coupler 56 is expanded to secure the female and male couplers 40, 56 to one another.

With reference to FIG. 7, the system 30 is advanced through a hollow anatomical structure (HAS), such as a vein, an artery, a gastric structure, a coronary structure, a pulmonary structure, or a tubular structure associated with a reproductive organ. For example, using standard techniques the operator may gain vascular access at an access site (e.g. the popliteal vein behind the knee, the femoral vein at the groin, or in the brachial vein in the arm) remote from the treatment site, and advance the system 30 toward the treatment site (e.g., the inferior vena cava, or any of the following veins: pelvic, isolated iliac, iliofemoral, isolated popliteal, isolated femoral, subclavian, or any other suitable vein or artery). For simplicity, remaining steps of the present method will be described with respect to a vascular procedure. However, it should be understood that the present embodiments are not limited to any particular procedure or location in the body.

The system 30 is preferably sized and configured to be received within the delivery sheath 76 and advanced through a patient's vasculature from a transcutaneous access site to a treatment site within the vasculature. Example dimensions for the delivery sheath 76 include an outside diameter of approximately 8 French, or in the range of 4 French to 12 French, and a length in the range of 50 cm-200 cm, or about 80 cm, or about 120 cm. External visualization, such as ultrasound or fluoroscopy, may be used to facilitate navigation through the vasculature.

Figure 3:
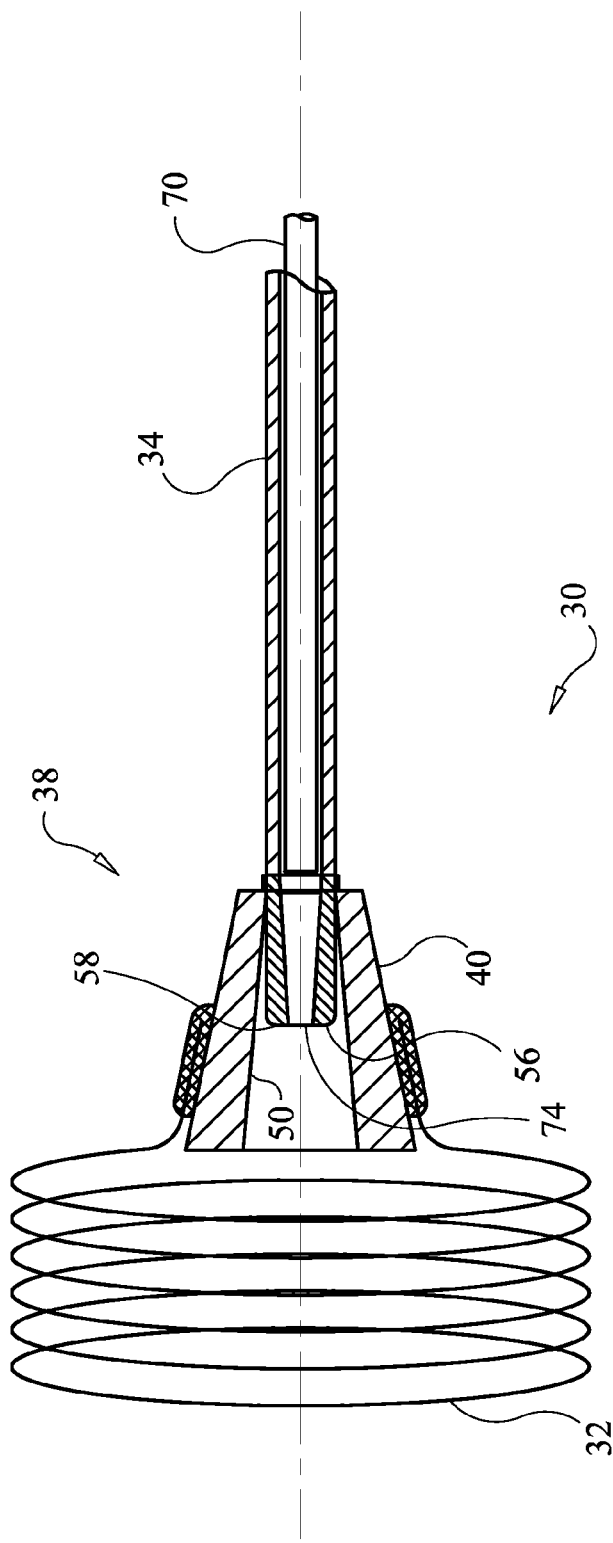
FIG. 3 is a schematic side elevation view of the system of FIG. 2, showing the male and female couplers in an engaged and unlocked position.
Figure 8:
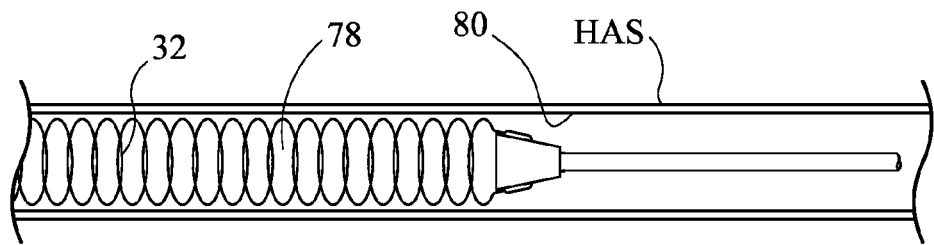
Figure 9:
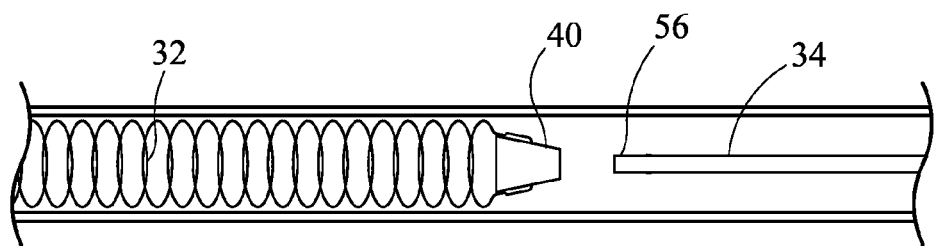

When the implant 32 reaches the treatment site, the delivery sheath 76 is withdrawn, as shown in FIG. 8. The self-expanding implant 32 expands to fill the HAS lumen 78 at the treatment site, and preferably bears against the inner wall 80 of the HAS with sufficient force to resist downstream migration. At this point, the operator may verify that the implant 32 is positioned as desired using external visualization. If so, the operator pulls back on the control member 70 at least until the control member 70 is located entirely proximally of the flexible legs 58 on the male coupler 56. As the control member 70 is withdrawn, the legs 58 of the male coupler 56 return to their original unstressed positions due to the return spring force in the flexed legs 58. This configuration is illustrated in FIG. 3. In this configuration, the operator pulls back on the delivery tube 34 to disengage the male coupler 56 from the female coupler 40, as shown in FIGS. 4 and 9. The delivery tube 34 and/or the control member 70 may include a marker (not shown) near its proximal end to alert the operator when the male coupler 56 has been completely withdrawn from the female coupler 40.

At this point, the operator may again verify that the implant 32 is positioned as desired using external visualization. If so, the operator may continue pulling back on the delivery tube 34 to completely withdraw the delivery tube 34 and the control member 70 from the vessel, leaving the implant 32 in the vessel. However, if the implant 32 is not positioned as desired, the operator may recapture and reposition the implant 32 by pushing the delivery tube 34 distally until the female and male couplers 40, 56 reengage (FIG. 3), and then pushing the control member 70 distally within the lumen 72 of the delivery tube 34 until the legs 58 of the male coupler 56 expand to capture the female coupler 40 (FIG. 4). More specifically, when the female and male couplers 40, 56 are reengaged as in FIG. 3, the control member 70 is advanced relative to the delivery tube 34 and the male coupler 56 so that the flexible legs 58 are pushed radially outward as the advancing control member 70 contacts the narrowing taper of the inner surfaces 62 of the flexible legs 58. The control member 70 continues to advance, and the legs 58 continue to be pushed radially outward, until the outer surfaces 64 of the legs 58 abut the inner surface 50 of the female coupler 40. In this configuration, the female and male couplers 40, 56 are secured to one another, due to the direction of taper on the female coupler 40, i.e. the proximal opening 54 is narrower than the distal opening 52 so that the radially expanded flexible legs 58 are wider than the proximal opening 54 and thus cannot be withdrawn through the proximal opening 54. Advantageously, the taper on the inner surface 50 of the female coupler 40 makes the recapture process "self-clinching." That is, even if the male coupler 56 has not been advanced completely into the female coupler 40 prior to advancing the control member 70, as the legs 58 on the male coupler 56 expand they will draw the female coupler 40 toward the male coupler 56 due to the taper.

With the implant 32 secured to the delivery tube 34, the operator may reposition the implant 32 by pushing or pulling the delivery tube 34 the desired distance, and then repeating the disengagement steps described above. Advantageously, the operator may reposition the implant 32 as many times as desired, due to the ease of disengaging/reengaging the female and male couplers 40, 56, and due to the linear spring characteristics of the legs 58 of the male coupler 56, i.e. no plastic deformation takes place within the legs 58 when they expand. Of course, after the implant 32 has been expelled from the delivery sheath 76, as described above, it may self-expand. Thus, to reposition the implant 32 the operator may advance the delivery sheath 76 relative to the expanded implant 32 to re-contract the implant 32.

Figure 10:
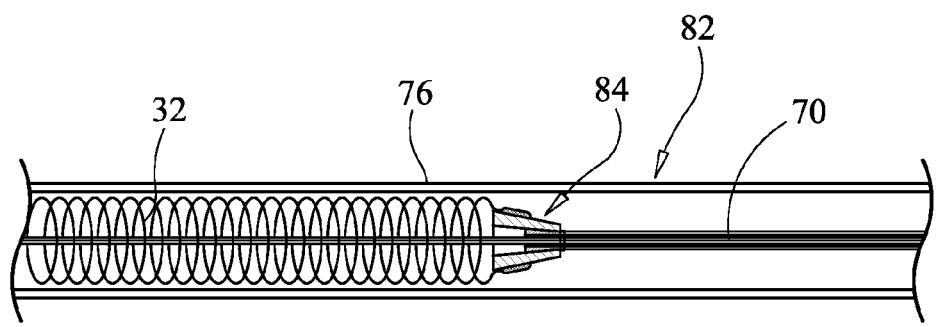
FIG. 10 is a schematic side elevation view of another embodiment of the present delivery systems for occlusive implants.

FIG. 10 illustrates another embodiment of a delivery system 82 for body implants 32. The system 82 is similar to the system 30 shown in FIGS. 1-4 and described above; therefore, common features will not be repeated here. In the embodiment of FIG. 10, the control member 70 extends through the coupler 84 and into the implant 32. Where the implant 32 is a tubular mesh coil, the control member 70 extending therethrough applies tension to the coil by bearing against a closed distal end of the coil. Typical tubular mesh coils have an at-rest internal diameter that can be reduced by applying longitudinally directed tension to the coil. That is, pulling on either end of the coil causes it to elongate and collapse radially. Releasing the tension causes the coil to spring back to its at-rest diameter. This tendency to spring back makes it difficult to push the tubular mesh coil into the delivery sheath 76, which preferably has as small a diameter as necessary to reach any given treatment site in the body. Extending the control member 70 through the coil so that it bears against a closed distal end of the coil applies tension to the coil, which radially collapses the coil, enhancing the ability to advance it into the delivery sheath 76 from the proximal end.

With the embodiment of FIG. 10, a method of deploying the implant 32 comprises the extra step of withdrawing the control member 70 from the implant 32. This step may be performed before or after the delivery sheath 76 is withdrawn, and may be performed in the same motion as withdrawing the control member 70 from the male coupler 56. Withdrawing the control member 70 from the implant 32 releases the support that the control member 70 provides for the implant 32, enabling the implant 32 to move toward its at-rest configuration (still constrained, however, by the delivery sheath 76 and/or the HAS).

Figure 11:
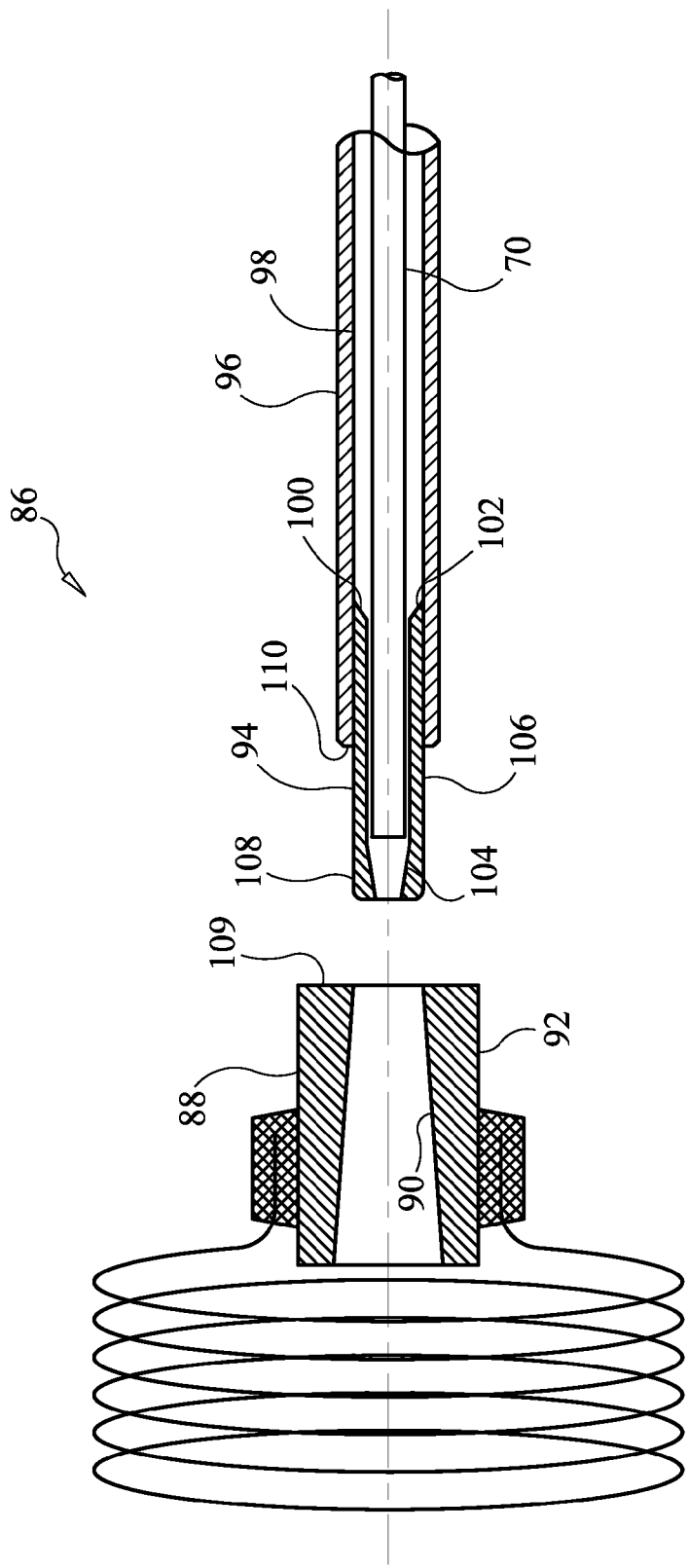
FIG. 11 is a schematic side elevation view of another embodiment of the present delivery systems for occlusive implants.

FIG. 11 illustrates another embodiment of a delivery system 86 for body implants. The system 86 is similar to the system 30 shown in FIGS. 1-4 and described above; therefore, common features will not be repeated here. In the embodiment of FIG. 11, the female coupler 88 is tubular, and includes an inner surface 90 having a smooth taper, with a diameter increasing in the proximal-to-distal direction. However, an outer surface 92 of the female coupler 88 may have a constant diameter.

With further reference to FIG. 11, the male coupler 94 is a tubular member that is received within a distal opening of the delivery tube 96. The male coupler 94 thus reduces the diameter of the lumen 98 in the delivery tube 96. A bevel 100 at the proximal end 102 of the male coupler 94 helps to guide the control member 70 into the lumen 104 of the male coupler 94, thus reducing the likelihood that control member 70 will jam against the male coupler 94 when pushed distally through the lumen 98 in the delivery tube 96.

The tubular male coupler 94 includes a constant outer diameter over its length. However, an inner diameter of the male coupler 94 varies over its length. In a proximal region 106, the inner diameter is constant, while in a distal region 108 the diameter smoothly tapers down to a narrower diameter in the proximal-to-distal direction. As in the embodiment of FIGS. 1-4, the taper angle of the male coupler 94 may be equal to the negative of the taper angle of the female coupler 88. As the control member 70 is pushed through the lumen 104 of the male coupler 94, the control member 70 engages the narrowing diameter in the distal region 108. The control member 70 is further advanced to bend the distal region 108 outward thereby engaging the tapering inner surface 90 of the female coupler 88, similar to the embodiment shown in FIGS. 1-4, described above.

An outer diameter of the male coupler 94 is slightly smaller than an inner diameter of the female coupler 88 at a proximal end 109 of the female coupler 88. A distal end 110 of the larger diameter delivery tube 96 thus forms a shoulder that acts as a position limiter. The distal end 110 is analogous to the position limiter 68 of the embodiment of FIGS. 1-4, and thus will not be further described here. Further, the operation of the system 86 of FIG. 11 to place an implant in an HAS is similar to the operation of the system 30 of FIGS. 1-4, and will also not be further described here.

Figure 12:
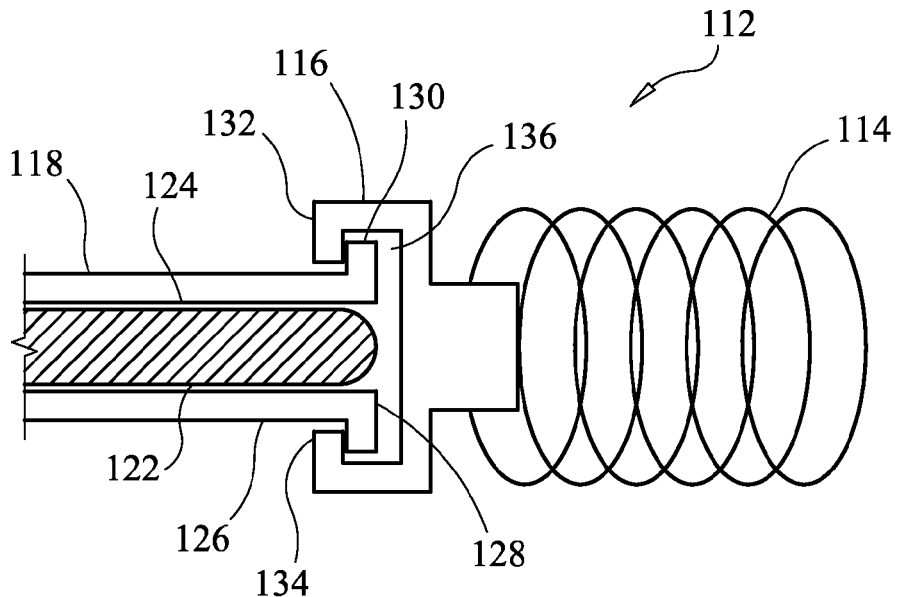
FIGS. 12 and 13 are schematic side elevation views of another embodiment of the present delivery systems for occlusive implants.
Figure 13:
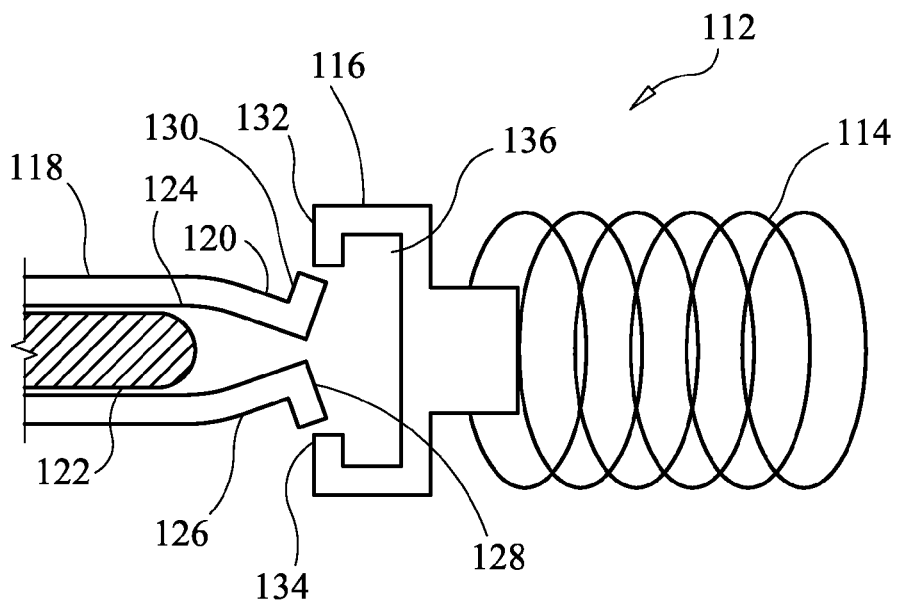

FIGS. 12 and 13 illustrate another embodiment of a delivery system 112 for body implants. As in the previous embodiments, the embodiment of FIGS. 12 and 13 includes an implant 114 with a female coupler 116 secured at a proximal end thereof, a delivery tube 118 having a male coupler 120 at a distal end thereof, and a control member 122 slidably received with a lumen 124 of the delivery tube 118. However, in contrast to the above embodiments, in the embodiment of FIGS. 12 and 13 the male coupler 120 includes legs 126 that are bowed inwardly in an at rest state (FIG. 13). The legs 126 may, for example, be heat set in order to achieve the inward bowing at rest.

Further, a distal end 128 of the male coupler 120 includes an outwardly extending flange 130, while a proximal end 132 of the female coupler 116 includes an inwardly extending flange 134 defining a receiving space 136. When the male coupler 120 is positioned in the receiving space 136, and the control member 122 is advanced distally to urge the legs 126 of the male coupler 120 outwardly (FIG. 12), the two flanges 130, 134 engage one another to lock the male coupler 120 and the female coupler 116 together. To release the female coupler 116 from the male coupler 120, the operator pulls back on the control member 122 until the legs 126 of the male coupler 120 flex inwardly a sufficient amount for the two flanges 130, 134 to clear one another. The operator then pulls back on the delivery tube 118 to draw the male coupler 120 out of the receiving space 136 (FIG. 13).

FIGS. 14 and 15 illustrate another embodiment of a delivery system 138 for body implants. With reference to FIG. 14, the female coupler 140 may include a proximal portion 142 having a first exterior diameter and a distal, portion 144 having a second exterior diameter, wherein the second exterior diameter is less than the first exterior diameter. The proximal and distal portions 142, 144 may meet at an external shoulder 146. The distal portion 144 may be received in a proximal end 148 of an implant 150, with the implant 150 abutting the shoulder 146. In alternative embodiments, the implant 150 may be spaced from the shoulder 146 or the exterior diameter may be constant.

The female coupler 140 further includes a stepped interior diameter, with a smaller interior diameter toward a proximal end 152 and a larger interior diameter toward a distal end 154. The smaller and larger interior diameter portions meet at an internal shoulder 156 that may be located closer to the proximal end 152 than the distal end 154. The internal shoulder 156 is oriented at a non-perpendicular angle with respect to a longitudinal axis of a delivery tube 158, and faces distally. As described below, the internal shoulder 156 provides a bearing surface for the male coupler 160 to lock the female and male couplers 140, 160 together.

With continued reference to FIG. 14, the system 138 further includes the delivery tube 158 having the male coupler 160 adjacent a distal end 159 of the delivery tube 158, such as being received within the distal end 159 of the delivery rube 158. With reference to FIG. 15, the male coupler 160 includes a reduced interior diameter portion 162 adjacent its distal end 164, wherein the interior diameter of the male coupler 160 abruptly decreases at a proximal-facing shoulder 166. The reduced interior diameter portion 162 may have a constant diameter over its length, which may be defined by the shoulder 166 at a proximal end and a chamfer 168 at a distal end. The reduced interior diameter portion 162 also defines expandable flexible legs 163. Similar to the expandable, flexible legs 58 described above. The distal end 159 of the delivery tube 158 bears against the proximal end 152 of the female coupler 140 when the female and male couplers 140, 160 are engaged with one another. The delivery tube 158 thus acts as a position limiter, limiting the extent to which the male coupler 160 may extend into the female coupler 140.

With reference to FIG. 15, the system 138 further includes a control member 170, which is similar to that described above with respect to the previous embodiments. An external diameter of the control member 170 is smaller than the internal diameter of the delivery tube 158 and the male coupler 160, except in the region of the reduced interior diameter portion 162, where the diameter of the control member 170 is greater than the diameter of the reduced interior diameter portion 162 of the male coupler 160. Thus, when the control member 170 is advanced, through the reduced interior diameter portion 162, the expandable legs 163 of the male coupler 160 bow outwardly, as shown in FIG. 14. A distal end 172 of the control member 170 may include a chamfer 174 about its periphery. The chamfer 174 provides a ramped surface to bear against the ramped surface of the shoulder 166 as the control member 170 is advanced past the shoulder 166. The engagement of the chamfer 174 and the shoulder 166 centers the control member 170 within the lumen 176 of the delivery tube 158 as the control member 170 advances past the shoulder 166, reducing the chance that the control member 170 will bind with the shoulder 166. A proximal end of the male coupler 160 further includes a chamfer 178 to center the control member 170 as it advances into the male coupler 160.

With reference to FIG. 14, the system 138 further includes a guide catheter 180 for receiving the delivery tube 158 and the implant 150 in a loose fitting fashion, such that the delivery tube 158 and the implant 150 can be readily moved proximally and distally within the catheter 180. For clarity, only a short section of the guide catheter 180 is shown. The catheter extends to the proximal end of the system 138, and distally over the implant 150 to compress it.

With further reference to FIG. 14, when the control member 170 extends through the male coupler 160, it forces the cantilevered expandable, flexible legs 163 radially outward. Exterior surfaces 182 of the legs 163 bear against the shoulder 156 on the female coupler 140, locking the two coupler portions 140, 160 together. With reference to FIG. 15, when the control member 170 is withdrawn such that it is entirely proximal of the reduced interior diameter portion 162, return spring forces in the cantilevered flexible legs 163 cause them to return to their unstressed positions, wherein they do not bow radially outward. The male coupler 160 can then be withdrawn from the female coupler 140, similarly as described above with respect to the previous embodiments.

Alternatively, the shoulder 156 of the female coupler 140 may be on the distal end 154 of the female coupler 140 and the interior diameter may be constant, such that the flexible legs 163 expand against the distal end 154 of the female coupler 140 to retain the female and male couplers 140, 160 together.

Figure 16:
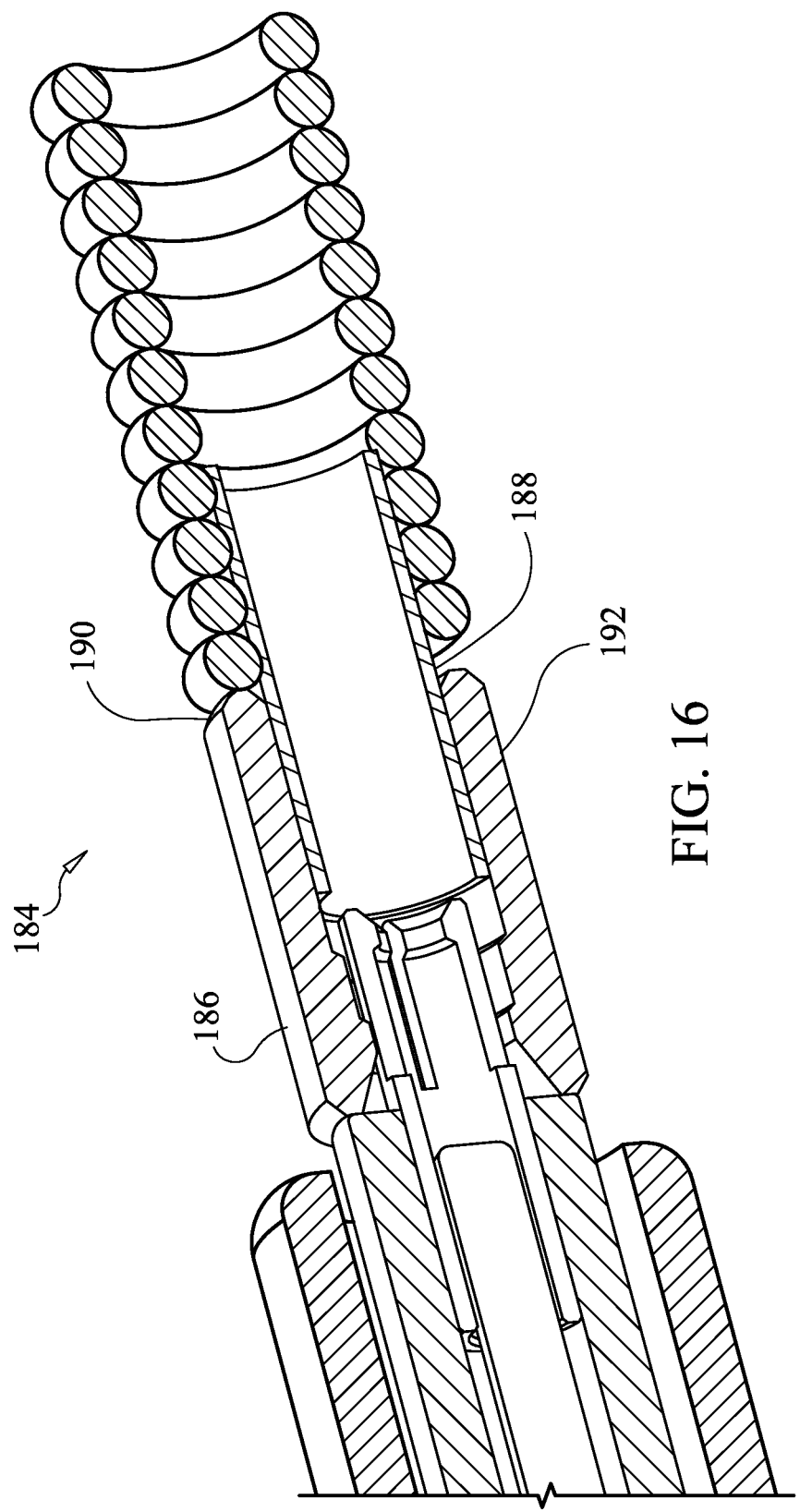
FIG. 16 is a side perspective cross-sectional view of another embodiment of the present delivery systems for occlusive implants, showing the male and female couplers in an engaged and unlocked position.

FIG. 16 illustrates another embodiment of a delivery system 184 for body implants. The system 184 of FIG. 16 is similar to the system 138 of FIGS. 14 and 15, except that the female coupler 186 is constructed of two discrete components: a distal portion 188 and a proximal portion 192. The distal portion 188 comprises a cylindrical sleeve that is received in a close fit: within a distal end 190 of the proximal portion 192 of the female coupler 186. The two components 188, 192 may be held together in a friction fit, or secured to one another as by welding or adhesive.

Figure 17:
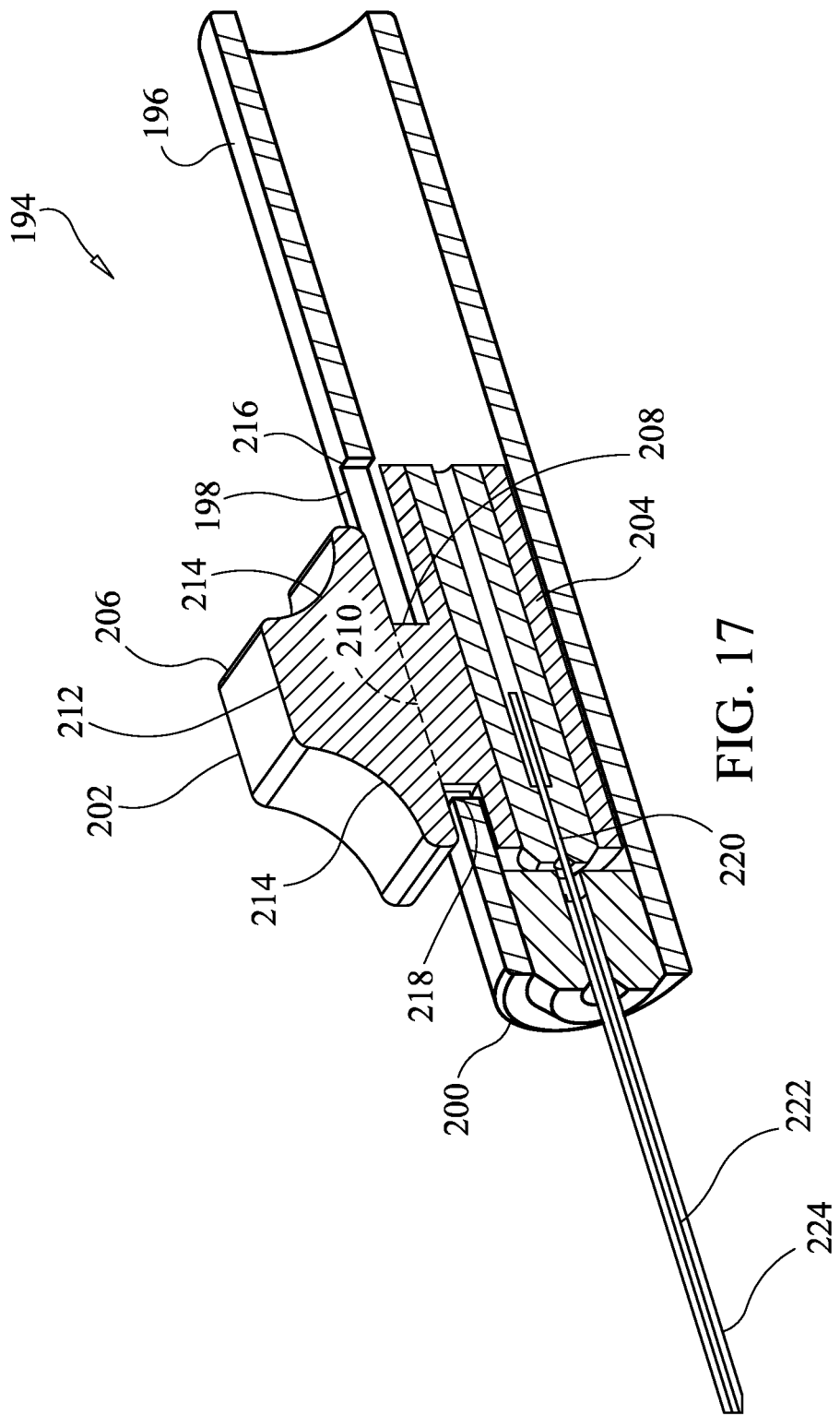
FIG. 17 is a side perspective cross-sectional view of one embodiment of a release handle configured for use with the present delivery systems for occlusive implants.

FIG. 17 illustrates one embodiment of a release handle 194 configured for use with the present delivery systems for occlusive implants. The handle 194 is located at a proximal end of the system, and includes a hollow housing 196 that functions as a grip, as described, below. In the illustrated embodiment, the housing 196 is cylindrical, but could have any shape, such as a pistol grip.

The housing 196 includes a longitudinal slot 198 adjacent a distal end 200. The slot 198 receives a sliding trigger 202. The trigger 202 includes a first portion 204 that is internal to the housing 196, a second portion 206 that is external to the housing 196, and a connecting portion 208 that extends through the slot 198 to connect the internal and external portions 204, 206. The internal portion 204 may be cylindrical, and has an external diameter that is less than an internal diameter of the housing 196, but preferably only slightly less to reduce play between the housing 196 and the trigger 202.

The connecting portion 208 may be shaped substantially as a rectangular parallelepiped, and extends radially outward from an outside surface of the internal portion 204 and through the slot 198. The external portion 206 may be shaped substantially as a trapezoid in profile, having a long edge 210 adjoining the connecting portion 208, a shorter parallel edge 212 spaced from the long edge 210, and concave edges 214 extending between ends of the long and short edges 210, 212.

A length of the connecting portion 208, when viewed in profile, is less than a length of the slot 198. The trigger 202 can thus translate proximally and distally with respect to the housing 196 between the proximal and distal ends 216, 218 of the slot 193. The internal portion 204 includes a passage 220 at a distal end thereof that receives the proximal end of a control member 222, similar to control members 70, 122 and 170 described above, in a friction fit. Thus, when the trigger 202 moves proximally and distally with respect to the housing 196, the control member 222 moves with it, thus translating the control member 222 proximally or distally with respect to a delivery tube 224 to lock and unlock the male and female couplers, as described above. In some embodiments, the release handle 194 may include a detent (not shown) corresponding to an unlocked position of the male and female couplers, so that the operator will receive a tactile indication that the couplers are unlocked. The detent may be located on the trigger 202 and/or the slot 198, for example.

To operate the release handle 194 of FIG. 17, an operator can grasp the housing 196 with one hand, and position his or her thumb on the sliding trigger 202. Applying light downward or inward pressure on the trigger 202, the operator can move his or her thumb proximally and distally to also move the trigger 202 and the control member 222 proximally and distally. From the distal-most position shown in FIG. 17, moving the trigger 202 proximally unlocks the male and female couplers, as described above. Conversely, from a proximal-most position (not shown), moving the trigger 202 distally locks the male and female couplers, as also described above. While not shown in FIG. 17, outwardly facing surfaces of the trigger external portion 206 may include roughness or texturing to enhance the ability of the operator to grip the trigger 202 with light thumb pressure.

Figure 18:
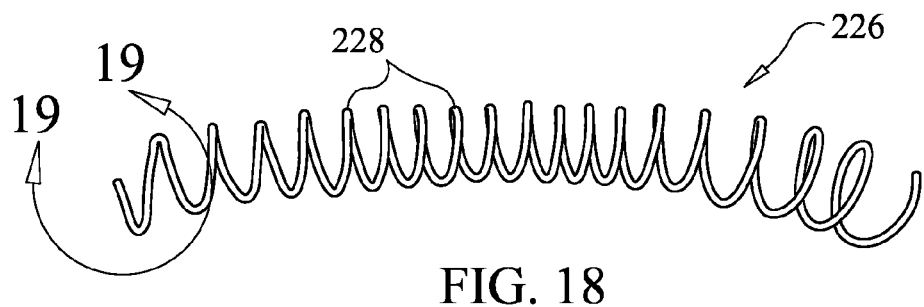
FIG. 18 is a schematic side elevation view of one embodiment of the present occlusive implants.
Figure 19:
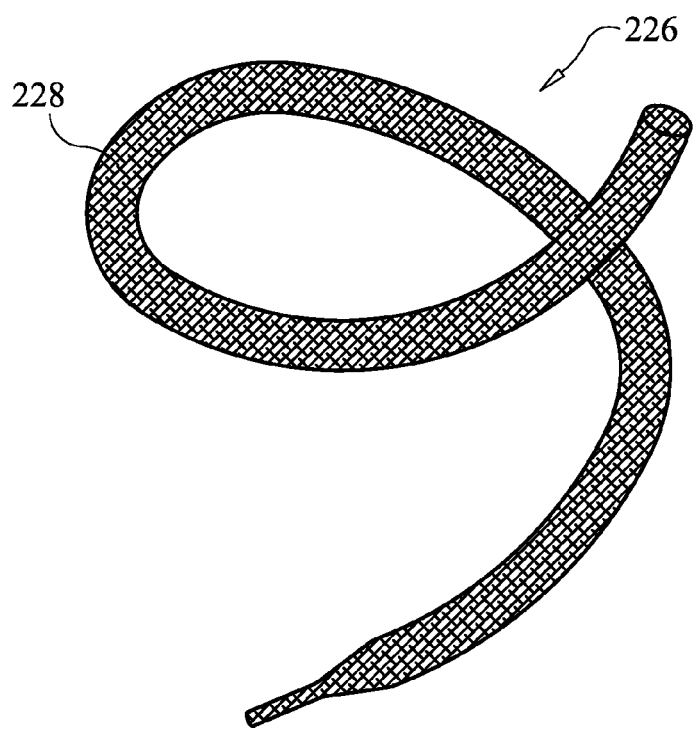
FIG. 19 is a detail view of the portion of FIG. 18 indicated by the circle 19-19.
Figure 20:
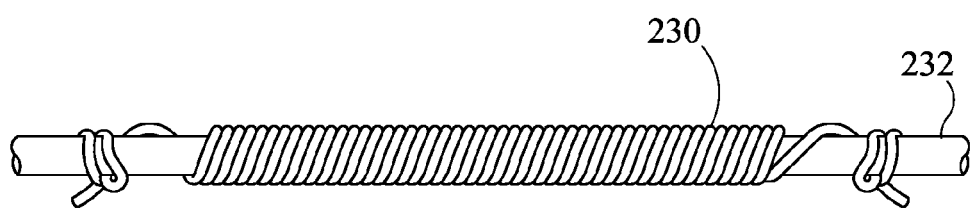
FIG. 20 is a schematic side elevation view of one embodiment of forming the occlusive implant of FIG. 18.

FIGS. 18 and 19 illustrate one embodiment of an occlusive implant 226 configured for use in the present systems for occluding HAS's. The implant 226 improves upon conventional coils by providing coils comprising tubular braided wire mesh. With reference to FIG. 18, the coil includes a plurality of helical winds 228. With reference to FIG. 19, each of the winds 228 comprises a tubular braided wire mesh. With reference to FIG. 20, one embodiment for forming the coiled mesh tube is to coil a length of straight mesh tube 230 tightly around a cylindrical mandrel 232, and then heat treat it according to known methods so that the formerly straight tube memorizes a coiled shape.

The mesh comprises a semi-permeable barrier made of connected strands of metal and shaped as a tube. In certain embodiments, the material of the mesh may be platinum (Pt), or a combination of Pt and cobalt-chrome (Co—Cr). Non-metals could also be used, such as polymers and resorbable poly(lactic-co-glycolic acid) (PLGA). Non-metal materials could be incorporate with one or more metals in the braid. Shape memory materials, such as nitinol (Ni—Ti), may be advantageous in maintaining a secondary tubular shape. However, it should be understood that any material could be used to make the mesh, and the foregoing examples are not limiting.

The tube is formed into a coil, as described above. When tension is applied at either end of the coiled tube, it straightens out and collapses down to a straight cylinder. The collapsed coil can be loaded into a catheter and delivered intravascularly to a treatment site, such as a location in a vessel to be occluded. When expelled from the catheter, the coil springs back to its unstressed shape. As described below, the present embodiments leverage the volume-filling advantage of tubular braided wire mesh, as opposed to conventional coils, to achieve greater efficiency in occluding hollow anatomical structures, such as vessels.

The following calculations illustrate the volume-filling advantage of the present tubular braided wire mesh over conventional coils. To calculate the volume of a conventional coil, it can be modeled as a solid cylinder. Then, its volume, V, is $$V = \Pi r^2 L, \text{ where}$$

r=radius of the cylinder, and
L=length of the cylinder.

Now, assuming the diameter of the coil is 0.02" and the length is 4", the volume is $$V = \Pi \left(\frac{0.02''}{2}\right)^2 \times 4 = 0.001256''$$

The diameter of the coil was selected as 0.02" because that is one common size for delivery catheters for conventional coils. Further, conventional coils do not expand upon being expelled from the delivery catheter. Thus, the deployed diameter of a conventional coil is equal to its diameter when loaded in the delivery catheter.

By contrast, a tubular braided wire mesh has a recovery factor of up to 4.5. That is, when a tubular braided wire mesh is expelled from a delivery catheter, it expands up to 4.5 times its diameter when constrained by the delivery catheter. Thus, to calculate the volume-filling capacity of a tubular braided wire mesh, the above calculation is repeated, but 0.09" is substituted for the diameter of the tubular braided wire mesh (4.5×0.002"). The volume is thus $$V = \Pi \left(\frac{0.09''}{2}\right)^2 \times 4 = 0.025434''$$

The volume-filling capacity of the tubular braided wire mesh is thus over twenty times that of a conventional coil per unit length $$\left(\left(\frac{0.025434''}{0.001256''}\right) = 20.25\right).$$

Thus, far fewer coiled wire mesh tubes are needed per unit length in order to occlude a vessel. This advantage can achieve significant cost savings, particularly where the occlusive implants are made of platinum, as is common with conventional coils.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. Apparatus for delivering an occlusive implant in a hollow anatomical structure, the apparatus comprising:
   an elongate flexible delivery tube having a proximal end and a distal end, and defining an internal delivery tube lumen having an inner lumen diameter;
   a male coupler at the distal end of the delivery tube and defining an internal male coupler lumen, the male coupler including a plurality of cantilevered flexible legs each including a distal end, each of the legs including an internal surface that defines at least a portion of the male coupler lumen and tapers inwardly toward the distal end of each leg such that an interior diameter of the male coupler lumen decreases in the proximal-to-distal direction; and
   an elongate control member received within the delivery tube lumen of the delivery tube and translatable therein proximally and distally, the control member having an outer diameter less than the inner lumen diameter of the internal delivery tube lumen and the internal male coupler lumen but greater than the interior diameter of the male coupler lumen adjacent the distal end of the legs, such that when the control member is advanced distally within the male coupler lumen the control member contacts the internal surfaces of the legs to cause them to flex outwardly, wherein the male coupler defines a constant outer diameter over its length without the control member contacting the internal surfaces of the legs to cause them to flex outwardly.

2. The apparatus of claim 1, wherein the control member extends distally of the male coupler to support the implant and resist deformation of the implant from a delivery configuration.

3. The apparatus of claim 1, wherein the male coupler is integral with the delivery tube.

4. The apparatus of claim 1, wherein the male coupler and the delivery tube are discrete components secured to one another.

5. The apparatus of claim 4, wherein a proximal portion of the male coupler is received within the internal delivery tube lumen of the delivery tube.

6. The apparatus of claim 5, wherein the legs of the male coupler extend distally of the delivery tube.

7. The apparatus of claim 5, wherein the distal end of the delivery tube comprises a position limiter configured to limit an extent of penetration of the male coupler into a female coupler of the implant.

8. The apparatus of claim 1, wherein the outer diameter of the male coupler is equal to an outer diameter of the delivery tube.

9. The apparatus of claim 1, further comprising a position limiter on an exterior of the delivery tube, the position limiter being configured to limit an extent of penetration of the male coupler into a female coupler of the implant.

10. A system for occluding a hollow anatomical structure, the system comprising:
   an occlusive implant including an occluding portion and a tubular female coupler, the female coupler defining a female coupler lumen whose internal diameter increases in the proximal-to-distal direction;
   an elongate flexible delivery tube defining a delivery tube lumen and having a distal end comprising a male coupler, the male coupler defining a male coupler lumen and including a plurality of cantilevered flexible legs configured to be received within the female coupler lumen, each of the legs including an internal surface that defines at least a portion of the male coupler lumen; and
   an elongate control member received within the delivery tube lumen and translatable therein proximally and distally, the control member having an outer diameter greater than an interior diameter of the male coupler lumen adjacent a distal end of the male coupler lumen, such that when the control member is advanced distally within the male coupler lumen the control member contacts the internal surfaces of the flexible legs to cause the flexible legs to flex outwardly and contact an inner surface of the female coupler lumen to releasably secure the implant to the delivery device,
   wherein an outer diameter of the male coupler is constant along its length without the control member contacting the internal surfaces of the flexible legs to cause the flexible legs to flex outwardly.

11. The system of claim 10, wherein the control member extends distally of the male coupler to support the implant and resist deformation of the implant from a delivery configuration.

12. The system of claim 10, wherein the implant is a braided mesh material shaped as a tubular coil.

13. The system of claim 10, wherein each of the legs includes an internal surface that tapers inwardly toward the distal end of each leg.

14. The system of claim 13, wherein a taper angle of the female coupler lumen matches a taper angle of the internal surface of the legs.

15. The system of claim 10, wherein the male coupler is integral with the delivery tube.

16. The system of claim 10, wherein the male coupler and the delivery tube are discrete components secured to one another.

17. The system of claim 10, wherein the outer diameter of the male coupler is equal to an outer diameter of the delivery tube.

18. The system of claim 10, further comprising a position limiter on an exterior of the delivery tube, the position limiter being configured to limit an extent of penetration of the male coupler into the female coupler.

19. The system of claim 10, wherein a proximal portion of the male coupler is received within the lumen of the delivery tube.

20. The system of claim 19, wherein the legs of the male coupler extend distally of the delivery tube.

21. The system of claim 19, wherein a distal end of the delivery tube comprises a position limiter configured to limit an extent of penetration of the male coupler into the female coupler.

22. A method for delivering an occlusive implant to a treatment site in a vessel of a body using an elongate flexible delivery device, the method comprising:
   accessing vasculature of the body at an access site remote from the treatment site;
   introducing the implant and the delivery device into the vasculature at the access site;
   advancing the implant and the delivery device through the vasculature toward the treatment site;
   positioning the implant at the treatment site;
   expanding the implant to contact an interior wall of the vessel and at least partially occlude the vessel;
   disengaging the implant from the delivery device; and
   withdrawing the delivery device;
   wherein the implant includes a tubular female coupler defining a female coupler lumen, the delivery device includes a distal end comprising a male coupler, and the male coupler is received within the female coupler lumen, the male coupler defining a male coupler lumen therethrough and including a plurality of cantilevered flexible legs extending distally,
   wherein disengaging the implant from the delivery device comprises withdrawing an elongate flexible control member received within a lumen of the delivery device and the male coupler lumen, the control member having an outer diameter greater than an interior diameter of the male coupler lumen at a distal end of the male coupler, such that as the control member is withdrawn from the male coupler lumen radially outwardly directed force is released from internal surfaces of the legs to cause the legs to relax and retract radially inwardly, and
   wherein an outer diameter of the male coupler is constant along its length when the elongate control member is withdrawn.

23. The method of claim 22, wherein expanding the implant comprises withdrawing an introducer sheath in which the implant is contained and compressed, thereby enabling the implant to self-expand.

24. The method of claim 22, wherein expanding the implant comprises withdrawing the control member from the implant, the control member, prior to its withdrawal, supporting the implant and resisting deformation of the implant from a delivery configuration.

25. The method of claim 22, wherein the implant is a braided mesh material shaped as a tubular coil.

26. The method of claim 22, wherein each of the legs includes an internal surface defining at least a portion of the male coupler lumen that tapers inwardly toward the distal end of each leg.

27. The method of claim 26, wherein the female coupler lumen is tapered and increases in diameter in the proximal-to-distal direction.

28. The method of claim 27, wherein a taper angle of the female coupler lumen matches a taper angle of the internal surface of the legs.

29. The method of claim 22, wherein the male coupler is integral with the delivery device.

30. The method of claim 22, wherein the male coupler and the delivery device are discrete components secured to one another.

31. The method of claim 22, wherein the outer diameter of the male coupler is equal to an outer diameter of the delivery device.

32. The method of claim 22, further comprising a position limiter on an exterior of the delivery device, the position limiter being configured to limit an extent of penetration of the male coupler into the female coupler.

33. The method of claim 22, wherein a proximal portion of the male coupler is received within the lumen of the delivery device.

34. The method of claim 33, wherein the legs of the male coupler extend distally of the delivery device.

35. The method of claim 33, wherein a distal end of the delivery device comprises a position limiter configured to limit an extent of penetration of the male coupler into the female coupler.

* * * * *